(12) United States Patent
Elisabettini et al.

(10) Patent No.: US 7,122,210 B2
(45) Date of Patent: Oct. 17, 2006

(54) BICARBONATE-BASED SOLUTIONS FOR DIALYSIS THERAPIES

(75) Inventors: Paola Elisabettini, Fleurus (BE); Jean-Paul Menneguerre, Burssels (BE); Jerome Colas, Brussels (BE); Christian Renaux, Germain-en Laye (FR); Jose Divino, Waterloo (BE); Dirk Faict, Assenede (BE); Isabelle Wilmet, Vieux-Genappe (BE)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 10/044,234

(22) Filed: Jan. 11, 2002

(65) Prior Publication Data

US 2003/0138501 A1 Jul. 24, 2003

(51) Int. Cl.
*A61P 7/08* (2006.01)
*A61K 33/00* (2006.01)
*A61K 33/14* (2006.01)

(52) U.S. Cl. .............. 424/717; 424/680; 424/722
(58) Field of Classification Search ............ 424/717, 424/722
See application file for complete search history.

(56) References Cited

U.S. PATENT DOCUMENTS

| | | | |
|---|---|---|---|
| 3,878,664 A | 4/1975 | Zinke | |
| 4,372,100 A | 2/1983 | Miller et al. | |
| 4,396,383 A | 8/1983 | Hart | |
| 4,397,392 A | 8/1983 | Runck et al. | |
| 4,465,488 A | 8/1984 | Richmond et al. | |
| 4,489,535 A | 12/1984 | Veltman | |
| 4,584,176 A | 4/1986 | Oliver et al. | |
| 4,630,727 A * | 12/1986 | Feriani et al. | 206/221 |
| 4,663,166 A | 5/1987 | Veech | |
| 4,756,838 A | 7/1988 | Veltman | |
| 4,761,237 A | 8/1988 | Alexander et al. | |
| 4,863,714 A | 9/1989 | Sovak et al. | |
| 4,879,280 A | 11/1989 | Seyffart et al. | |
| 4,959,175 A | 9/1990 | Yatzidis | |
| 5,011,826 A | 4/1991 | Steudle et al. | |
| 5,039,609 A | 8/1991 | Klein | |
| 5,092,838 A | 3/1992 | Faict et al. | |
| 5,122,516 A * | 6/1992 | Watanabe et al. | 514/23 |
| 5,141,492 A | 8/1992 | Dadson et al. | |
| 5,211,643 A | 5/1993 | Reinhardt et al. | |
| 5,296,242 A | 3/1994 | Zander | |
| 5,383,324 A | 1/1995 | Segers et al. | |
| 5,423,421 A | 6/1995 | Inoue et al. | |
| 5,431,496 A | 7/1995 | Balteau et al. | |
| 5,462,526 A | 10/1995 | Barney et al. | |
| 5,509,898 A | 4/1996 | Isono et al. | |
| 5,536,469 A | 7/1996 | Jonsson et al. | |
| 5,560,403 A | 10/1996 | Balteau et al. | |
| 5,601,730 A | 2/1997 | Page et al. | |
| 5,610,170 A | 3/1997 | Inoue et al. | |
| 5,616,248 A | 4/1997 | Schal | |
| 5,706,937 A | 1/1998 | Futagawa et al. | |
| 5,827,820 A | 10/1998 | duMoulin et al. | |
| 5,853,388 A | 12/1998 | Semel | |
| 5,871,477 A * | 2/1999 | Isono et al. | 604/410 |
| 5,945,129 A | 8/1999 | Knerr et al. | |
| 6,013,294 A | 1/2000 | Bunke et al. | |
| 6,139,754 A | 10/2000 | Hartranft et al. | |

FOREIGN PATENT DOCUMENTS

| | | |
|---|---|---|
| DE | 19748290 | 5/1999 |
| EP | 0 083 360 | 7/1983 |
| EP | 0 165 933 B1 | 1/1986 |
| EP | 0 209 607 | 1/1987 |
| EP | 0 249 667 B1 | 12/1987 |
| EP | 0 277 868 A2 | 8/1988 |
| EP | 0 278 100 A2 | 8/1988 |
| EP | 0 399 549 A1 | 11/1990 |
| EP | 0 399 918 A2 | 11/1990 |
| EP | 0 417 478 A1 | 3/1991 |
| EP | 0 437 274 A1 | 7/1991 |
| EP | 0 439 061 B1 | 7/1991 |
| EP | 0 481 257 A1 | 4/1992 |
| EP | 0602014 | 6/1994 |
| EP | 0 613 688 A1 | 9/1994 |
| EP | 0 647 145 B1 | 4/1995 |
| EP | 0 776 649 A2 | 6/1997 |
| EP | 0 935 967 A2 | 8/1999 |
| EP | 1166787 | 1/2002 |
| FR | 2 753 099 | 3/1998 |
| JP | 56164113 | 12/1981 |
| JP | 2304026 | 12/1990 |

(Continued)

OTHER PUBLICATIONS van Bommel et al., *Continuous Renal Replacement Therapy for Critically III Patients: An Update*, Journal of Intensive Care Medicine, vol. 9, No. 6, Nov.-Dec. 1994, pp. 265-280.

(Continued)

*Primary Examiner*—Johann Richter
*Assistant Examiner*—Frank Choi
(74) *Attorney, Agent, or Firm*—Paula J. F. Kelly; Robert M. Barrett

(57) ABSTRACT

Bicarbonate containing solutions for use during medical treatment are provided. The bicarbonate containing solution of the present invention includes at least two separate components including a bicarbonate concentrate and an electrolyte concentrate which can be readily and sterilely mixed to form a ready-to-use formulation for patient administration, particularly as applied to the treatment of acute renal failure associated with critically ill patients in an intensive care setting.

11 Claims, 1 Drawing Sheet

FOREIGN PATENT DOCUMENTS

| | | |
|---|---|---|
| JP | 3195561 | 8/1991 |
| JP | 5105633 | 4/1993 |
| JP | 8131542 | 5/1993 |
| JP | 6105905 | 4/1994 |
| JP | 7252137 | 10/1995 |
| JP | 8164199 | 6/1996 |
| JP | 9087182 | 3/1997 |
| JP | 9110703 | 4/1997 |
| JP | 9301875 | 11/1997 |
| JP | 10201821 | 8/1998 |
| JP | 11-9659 | 1/1999 |
| JP | 11-19178 | 1/1999 |
| JP | 11004872 | 1/1999 |
| WO | WO 86/03407 | 6/1986 |
| WO | WO 87/03809 | 7/1987 |
| WO | WO 91/18610 | 12/1991 |
| WO | WO 95/19778 | 7/1995 |
| WO | WO 96/01118 | 1/1996 |
| WO | WO 97/05851 | 2/1997 |
| WO | WO 98/10733 | 3/1998 |
| WO | WO 99/01144 | 1/1999 |
| WO | WO 99/09953 | 3/1999 |
| WO | WO 01/17534 | 3/2001 |

OTHER PUBLICATIONS

S. Uthoff et al., *Improved Correction of Acidosis in Acute Renal Failure Using a Bicarbonate Buffered Substitution Solution*, Nephrology (1997), Suppl. 1, p. 1598.

A. N. Thomas et al, *Comparison of lactate and bicarbonate buffered haemofiltration fluids: use in critically ill patients*, Nephrology Dialysis Transplantation, (1997), vol. 12, pp. 1212-1217.

Manns et al., *Continuous Renal Replacement Therapies: An Update*, American Journal of Kidney Diseases, vol. 32, No. 2 (Aug.) 1998; pp. 185-207.

Feriani et al., *Acid-base balance and replacement solutions in continuous renal replacement therapies*, Kidney International, vol. 53, Suppl. 66 (1998), pp. S-156-S-159.

Heering et al., *The use of different buffers during continuous hemofiltration in critically ill patients with acute renal failure*, Intensive Care Medical (1999) vol. 25, pp. 1244-1251.

Zimmerman et al., *Continuous veno-venous haemodialysis with a novel bicarbonate dialysis solution: prospective cross-over comparison with a lactate buffered solution*, Nephrology Dialysis Transplantation, (1999) vol. 14, pp. 2387-2391.

Heering et al., *Acid-base balance and substitution fluid during continuous hemofiltration*, Kidney International, vol. 56, Suppl. 72 (1999) pp. S-37-S-40.

Lutkes et al., *Continuous venovenous hemodialysis treatment in critically ill patients after liver transplantation*, Kidney International, vol. 56 Suppl. 72 (1999) pp. S-71-S-74.

Kierdorf et al., *Lactate- or bicarbonate-buffered solutions in continuous extracorporeal renal replacement therapies*, Kidney International, vol. 56, Suppl. 72 (1999) pp. S-32-S-36.

Barenbrock et al., *Effects of bicarbonate- and lactate-buffered replacement fluids on cardiovascular outcome in CVVH patients*, Kidney International, vol. 58 (2000) pp. 1751-1757.

Manahan et al., *Peritoneal Dialysis using bicarbonate-containing solution sterilized by ultrafiltration*, The International Journal of Artificial Organs, vol. 14 No. 8, 1999, pp. 463-465.

Murphy et al., *Use of an Artificial Kidney*, vol. 40, 1952, pp. 436-444.

Tjiang, Boen San, *A Clinical Study of Factors Governing its Effectiveness*, Peritoneal Dialysis, p. 76, Van Gorcum & Co., Assen, The Neterlands (1959).

Feriani et al., *Short-Term Clinical Study with Bicarbonate-Containing Peritoneal Dialysis Solution*, Peritoneal Dialysis International, vol. 13, pp. 296-301 (1993).

*The Merck Index*, 12th Ed., Merck Research Laboratories, Whitehouse Station, NJ, 9 1472 (1996).

Odel et al., *Peritoneal Lavage as an Effective Means of Extraenal Excretion. A Clinical Appraisal*, American Journal of Medicine, vol. 9, 63-88 (1950).

Schambye et al., *The Cytotoxicity of Continuous Ambulatory Peritoneal Dialysis Solutions with Different Bicarbonate/Lactate Ratios*, Peritoneal Dialysis International vol. 13, Suppl. 2, Oct. 1-4, pp. S116-S118 (1994).

Schambye et al., *Bicarbonate-versus Lactate-Based CAPD fluids: A Biocompatibility Study in Rabbits*, Peritoneal Dialysis International, vol. 12, pp. 281-286 (1992).

Simonsen et al., *Less Infusion Pain and Elevated Level of Cancer Antigen 125 by the Use of a New and More Biocompatible PD Fluid*, Advances in Peritoneal Dialysis, vol. 12, pp. 156-160 (1996).

Ing., et al., *Bicarbonate-Buffered Peritoneal Dialysis*, The International Journal of Artificial Organ, vol. 8, No. 3, p. 121-124 (1985).

Zhou et al., *Effects of an Acidic, Lactate-Based Peritoneal Dialysis Solution and its Euhydric, Bicarbonate-Based Counterpart on Neutrophilic Interacellular pH*, Int. J. Artif. Organs, vol. 16, No. 12, pp. 816-819 (1993).

American Society for Artificial Internal Organs, 1994 Abstracts, pp. 110.

Faller et al., *Loss of Ultrafiltration in Continuous Ambulatory Peritoneal Dialysis: A Role for Acetate*, Peritoneal Dialysis Bulletin, Jan.-Mar. 1984, pp. 10-13.

Ing et al., *Lactate-Containing Peritoneal Dialysis Solutions*, International J. of Artificial Organs, vol. 16, No. 10, 1993, pp. 688-693.

Ing et al., *Lactate-Containing Versus Bicarbonate-Containing Peritoneal Dialysis Solutions*, Peritoneal Dialysis International, vol. 12, pp. 276-277.

Ing et al., *Preparation of Bicarbonate-Containing Dialysate for Peritoneal Dialysis*, International J. of Artificial Organs, vol. 6, No. 4, 1983, pp. 217-218.

Manahan et al., *Effects of Bicarbonate-Containing Versus Lactate-Containing Peritoneal Dialysis Solutions on Superoxide Production by Human Neutrophils*, Artificial Organs, vol. 13, No. 6, 1989, pp. 495-497.

Richardson et al., *Bicarbonate, L-Lactate, and D-Lactate Balance in Intermittent Peritoneal Dialysis*, Peritoneal Dialysis Bulletin, vol. 6, No. 4, 1986, pp. 178-185.

Yatzidis, Hippocrates, *A New Stable Bicarbonate Dialysis Solution for Peritoneal Dialysis: Preliminary Report*, Peritoneal Dialysis International, vol. 11, pp. 224-227.

\* cited by examiner

BICARBONATE-BASED SOLUTIONS FOR DIALYSIS THERAPIES

BACKGROUND OF THE INVENTION

The present invention relates generally to medical treatments. More specifically, the present invention relates to bicarbonate-based solutions for use during dialysis therapies, such as continuous renal replacement therapies.

A variety of different medical treatments are known and used to treat critically ill patients for acute renal failure (ARF) which is typically associated with multiple organ failure syndrome in intensive care settings. For example, traditional dialysis therapies, such as hemodialysis and peritoneal dialysis, are commonly used to treat ARF.

However, because traditional dialysis therapies are known to have limited use with respect to the treatment of critically ill patients for ARF, the use of continuous renal replacement therapy in favor of traditional dialysis therapies has increased, particularly in intensive care settings. In this regard, a number of possible advantages with respect to CRRT in comparison to traditional dialysis therapies have been recognized.

A foremost advantage is the potential to effectively avoid, or at least minimize, cardiovascular instability. In this regard, CRRT, in general, is a slow and continuous therapy that does not include rapid shifts in blood volume and electrolyte concentration due to the removal of metabolic products from blood as compared to traditional forms of dialysis therapy, such as hemodialysis. Examples of continuous renal replacement therapies include continuous arteriovenous hemofiltration, continuous arteriovenous hemodiafiltration, continuous venovenous hemofiltration, continuous venovenous hemodiafiltration, slow continuous ultrafiltration and continuous ultrafiltration periodic intermittent hemodialysis.

In general, CRRT is a convective blood cleansing technique that utilizes a patient's blood pressure as the primary driving force for ultrafiltration. During CRRT therapy, blood typically flows through a hemofilter such that a transmembrane pressure gradient between the blood compartment and the ultrafiltrate compartment causes plasma water to be filtered across the highly permeable membrane. As the water crosses the membrane, it can convect small and large molecules across the membrane and thus cleanse the blood.

An excessive amount of plasma water is also removed during continuous renal replacement therapy. In order to maintain a proper water balance in the patient's body, fluid must be substituted continuously by a balanced electrolyte solution (replacement or substitution fluid). The substitution fluid can be infused intravenously either into the arterial blood line leading to the hemofilter (predilution) or into the venous blood line leaving the hemofilter (post dilution).

Typically, commercially available replacement fluids are lactate-based solutions. However, the physiological buffer bicarbonate is preferred over lactate in patients with multiple organ failure which is typically associated with ARF. In this regard, the metabolic conversion of lactate to bicarbonate is not required prior to metabolic action thus eliminating undesirable effects due to the conversion process of lactate to bicarbonate.

Further, it is common practice among intensive care physicians to manually prepare solutions buffered with bicarbonate extemporaneously. This is typically carried out by adding the prepared bicarbonate solution to an existing sterile solution to form the bicarbonate-based solution prior to administration to the patient. For example, it is known to add bicarbonate to an acidic electrolyte concentrate solution which is in direct contact with administration tubing connected to the patient prior to administration thereof to the patient. It is also common practice to manually inject other electrolytes, such as potassium chloride, directly and separately into the bicarbonate-based solution prior to administration.

However, the physical handling due to the initial preparation of a bicarbonate solution, subsequent addition thereof to another solution and manual injection of other components to form the resultant bicarbonate-based solution prior to administration may be too tedious and time-consuming to adequately address the time-sensitive nature of responding to ARF in an intensive care setting. This practice may also necessarily cause the bicarbonate to degrade into a volatile carbon dioxide gas and a carbonate ion, which then can react with calcium and magnesium ions in solution to undesirably form precipitates, thus impeding proper administration. Further, the potential of bacteriological contamination of the bicarbonate-based solution is great unless strict aseptic techniques are followed during preparation.

A need, therefore, exists to provide improved bicarbonate-based solutions that can be effectively administered during continuous renal replacement therapy to treat ARF, particularly as administered to critically ill patients in an intensive care setting.

SUMMARY OF THE INVENTION

The present invention provides improved bicarbonate containing solutions that can be effectively administered during dialysis therapy, such as continuous renal replacement therapy. The bicarbonate containing solution of the present invention includes at least two separate components including a bicarbonate concentrate and an electrolyte concentrate which can be readily and sterilely mixed to form a ready-to-use formulation for patient administration, particularly as applied to treat acute renal failure associated with critically ill patients in an intensive care setting.

In an embodiment, a two part dialysis solution is provided. The two part dialysis solution at least includes a first component and a second component. The first component at least includes a bicarbonate concentrate and the second component at least includes an electrolyte concentrate. The first and second components can include a variety of other suitable constituents to ensure that the first and second components can be readily and sterilely mixed to form ready-to-use formulations.

For example, the first and second components, in an embodiment, each include physiological acceptable amounts of sodium, such as an amount of 160 mmol/L or less. In an embodiment, the first and second components each include physiological acceptable amounts of potassium, such as an amount that ranges from about 0.1 mmol/L to about 5 mmol/L. Alternatively, the first component which contains the bicarbonate concentrate does not include potassium where the second component does include potassium.

The ready-to-use formulations of the present invention can be prepared in a number of suitable ways. In an embodiment, the first and second components are separately stored from each other, such as in separate and hydraulically connected chambers of a multi-chamber container, until mixed together to form a mixed solution. In this regard, the ready-to-use formulation can be prepared within the container by mixing its two components within one chamber of the container. This can effectively eliminate the need to manually inject all or at least a portion of the components into the container to form the mixed solution, thus ensuring that the ready-to-use formulation can be readily prepared under sterile conditions.

Further, the container can be configured such that one of the components can be placed in direct fluid communication with the patient prior to mixing while the other component cannot be placed in direct fluid communication with the patient prior to mixing. This can provide an added level of safety with respect to the preparation and administration of the ready-to-use formulation of the present invention as the component that cannot be placed in direct fluid communication with the patient physically cannot be fed to the patient unless it is first mixed with the other component. In this regard, if, by chance, the component that physically cannot be placed in direct fluid communication with the patient were to have an undesirable concentration of constituents, such as potassium, sodium or the like, this configuration would necessarily ensure that the undesirable level of constituents is not fed or administered to the patient.

In another embodiment, the present invention provides a method of providing hemofiltration. The method includes the steps of providing a first component and a second components as previously discussed, mixing the first and second components to form a mixed solution and using the mixed solution during hemofiltration.

In an embodiment, the mixed solution is used as a dialysate. Alternatively, in an embodiment, the mixed solution is administered as an infusion solution during continuous renal replacement therapy.

An advantage of the present invention is to provide improved bicarbonate-based solutions.

Another advantage of the present invention is to provide improved bicarbonate containing solutions which include a number of components, such as an electrolyte concentrate and a bicarbonate concentrate, that can be readily and sterilely mixed to form a ready-to-use formulation suitable for administration to a patient during medical therapy including dialysis therapy.

Still another advantage of the present invention is to provide improved systems and methods for providing bicarbonate-based solutions to patients during dialysis therapy.

Yet another advantage of the present invention is to provide medical treatments that employ improved bicarbonate-based solutions to treat, for example, acute renal failure during continuous renal replacement therapy.

A further advantage of the present invention is to provide two-part bicarbonate containing solutions that can be readily and sterilely formed to facilitate their use during medical therapy, particularly in an intensive care setting.

A still further advantage of the present invention is to provide a multi-chamber container that separately houses bicarbonate and electrolyte concentrates such that ready-to-use bicarbonate based formulations can be prepared by mixing the bicarbonate and electrolyte concentrates in the multi-chamber container thereby effectively eliminating the need to add one or more components, such as potassium chloride, to the bicarbonate based formulation via manual injection.

Additional features and advantages of the present invention are described in, and will be apparent from, the following detailed description of the invention and the figures.

DETAILED DESCRIPTION OF THE INVENTION

Figure 1:
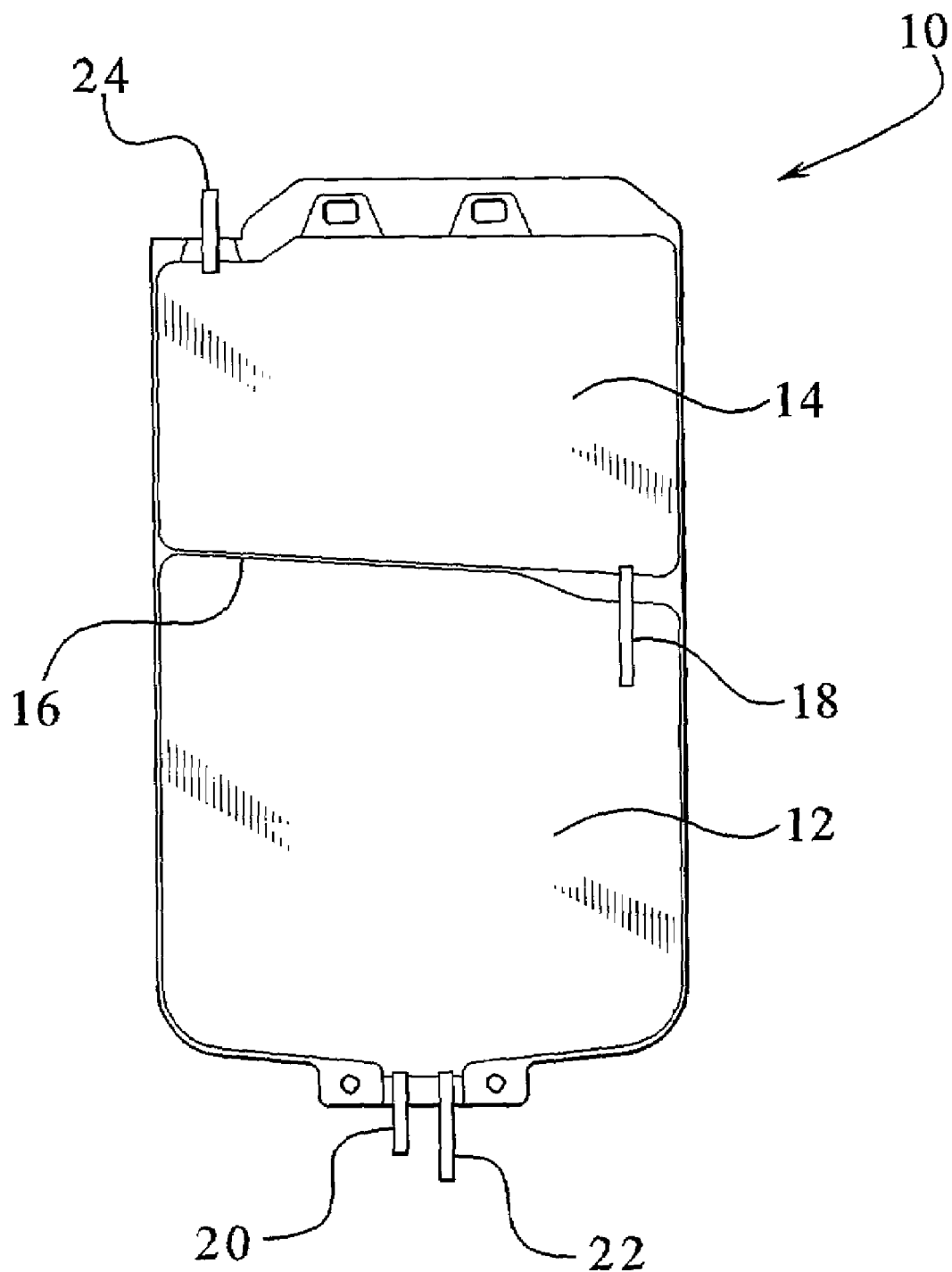
FIG. 1 illustrates a multi-chamber bag for storing a bicarbonate containing solution made pursuant to the present invention.

The present invention provides improved bicarbonate-based solutions that can be effectively administered to a patient during medical therapy, particularly dialysis therapy. The bicarbonate containing solution of the present invention includes at least two separate components including a bicarbonate concentrate and an electrolyte concentrate which can be readily and sterilely mixed to form a ready-to-use formulation for patient administration. The bicarbonate-based solution can be effectively utilized in a number of different medical applications including, for example, dialysis therapy.

With respect to dialysis therapy, the present invention can be used in a variety of different dialysis therapies to treat kidney failure. Dialysis therapy as the term or like terms are used throughout the text is meant to include and encompass any and all forms of therapies that utilize the patient's blood to remove waste, toxins and excess water from the patient. Such therapies, such as hemodialysis, hemofiltration and hemodiafiltration, include both intermittent therapies and continuous therapies used for continuous renal replacement therapy (CRRT). The continuous therapies include, for example, slow continuous ultrafiltration (SCUF), continuous venovenous hemofiltration (CVVH), continuous venovenous hemodialysis (CVVHD), continuous venovenous hemodiafiltration (CVVHDF), continuous arteriovenous hemofiltration (CAVH), continuous arteriovenous hemodialysis (CAVHD), continuous arteriovenous hemodiafiltration (CAVHDF), continuous ultrafiltration periodic intermittent hemodialysis or the like. Further, although the present invention, in an embodiment, can be utilized in methods providing a dialysis therapy for patients having chronic kidney failure or disease, it should be appreciated that the present invention can be used for acute dialysis needs, for example, in an emergency room setting. Lastly, as one of skill in the art appreciates, the intermittent forms of therapy (i.e., hemofiltration, hemodialysis and hemodiafiltration) may be used in the in center, self/limited care as well as the home settings.

In an embodiment, the bicarbonate-based solution can be used as a dialysate during any suitable dialysis therapy. In an embodiment, the solutions of the present invention can be administered or infused to a patient as a replacement solution, infusion solution or the like during dialysis therapy, particularly during continuous renal replacement therapy. As previously discussed, replacement solutions, infusion solutions or the like must necessarily be continuously fed to a patient as a substitute for an excessive amount of plasma water that is typically removed during continuous renal replacement therapy. In this regard, a proper water balance in the patient's body can be effectively maintained.

In an embodiment, the bicarbonate-based solution includes sodium ($Na^+$), calcium ($Ca^{++}$), magnesium ($Mg^{++}$), potassium ($K^+$), bicarbonate ($HCO_3^-$), chloride ($Cl^-$), lactate ($CH_3CHOHCOO^-$), acetate ($CH_3COO^-$), anhydrous glucose or dextrose, hydrous glucose or dextrose, like constituents and combinations thereof. The solution can include any suitable and physiological acceptable and effective amounts of the constituents. The term "physiological acceptable" as used herein means any suitable amount of a constituent or constituents of the bicarbonate based solution of the present invention (e.g., potassium, sodium or the like) that can be administered to a patient in a safe, acceptable and/or tolerable manner.

In an embodiment, the solution includes about 100 mmol/L to about 160 mmol/L of sodium, preferably about 130 mmol/L to about 150 mmol/L of sodium; about 0 mmol/L to about 2.0 mmol/L of calcium, preferably about 0 mmol/L to about 1.75 mmol/L of calcium, more preferably about 0.2 mmol/L to about 2.0 mmol/L of calcium; about 0 mmol/L to about 1.5 mmol/L of magnesium, preferably about 0.25 mmol/L to about 0.75 mmol/L of magnesium; about 0 mmol/L to about 5 mmol/L of potassium, preferably about 0 mmol/L to about 4 mmol/L of potassium; about 20 mmol/L to about 45 mmol/L of bicarbonate, preferably about 25 mmol/L to about 35 mmol/L of bicarbonate; about 70 mmol/L to about 130 mmol/L of chloride, preferably about 70 mmol/L to about 120 mmol/L of chloride, more preferably about 91 mmol/L to about 128 mmol/L of chloride; about 0 mmol/L to about 45 mmol/L of lactate, preferably about 0 mmol/L to about 35 mmol/L of lactate; about 0 mmol/L to about 45 mmol/L of acetate, preferably about 0 mmol/L to about 35 mmol/L of acetate; about 0 g/L to about 2.5 g/L glucose, preferably about 0 g/L to about 2.0 g/L of glucose; or combinations thereof. Applicants have found that the bicarbonate-based solutions of the present invention are stable for over a six month period at a physiological acceptable pH ranging from about 6.5 to about 8.0 at 25° C., preferably at a pH ranging from about 7.1 to about 7.4.

As previously discussed, the bicarbonate-based solution of the present invention includes a number of constituents or components that are separately housed such that the components can be readily and sterilely mixed to form the resulting bicarbonate-based solution. Applicants have discovered that the bicarbonate-based solution of the present invention can eliminate the need of excessive handling of one or more of its components prior to mixing as compared to conventional solutions which necessarily require a physician or other medical care provider to manually inject one or more components, such as bicarbonate, potassium chloride and the like, during the formulation of the bicarbonate solution.

In this regard, the ready-to-use bicarbonate-based formulations of the present invention can decrease the amount of time and effort with respect to the preparation and administration of the formulations of the present invention as compared to conventional bicarbonate formulations. The ready-to-use formulations of the present invention can also effectively eliminate, or at least greatly minimize, the potential of the spread of biological contamination during the preparation, administration and/or general use thereof. Such attributes of the bicarbonate-based formulations of the present invention are desirable as applied to medical therapies, particularly in an intensive care setting.

It should be appreciated that the components of the solution can be housed or contained in any suitable manner such that the bicarbonate-based solutions of the present invention can be effectively prepared and administered. In an embodiment, the present invention includes a two part bicarbonate-containing solution in which each part or component are formulated and stored separately, and then mixed just prior to use. A variety of containers can be used to house the two part bicarbonate-containing solution, such as separate containers (i.e., flasks or bags) that are connected by a suitable fluid communication mechanism. In an embodiment, a multi-chamber container or bag can be used to house the separate components of the solution.

FIG. 1 illustrates a suitable container for storing, formulating and administering a bicarbonate-based solution of the present invention. The multi-chamber bag 10 has a first chamber 12 and a second chamber 14. The interior of the container is divided by a heat seal 16 into two chambers. It should be appreciated that the container can be divided into separate chambers by any suitable seal. In an embodiment, the container can be divided into separate chambers, such as two chambers, by a peel seal. The multi-chamber container 10 also has a frangible connector 18 to sealingly couple the first chamber 12 to the second chamber 4. To mix the solution within the multi-chamber bag 10, the frangible connector 18 is broken.

The first container or chamber 12 includes two port tubes having, for example, different lengths. As shown in FIG. 1, the short port tube 20 can be utilized to add other constituents to the first chamber 12 during formulation of the solution of the present invention, if necessary. The long port tube 22 can be utilized to adaptedly couple the first chamber 12 to the patient via, for example, a patient's administration line (not shown). The second container or chamber 14 has a single port tube 24 extending therefrom which is closed by, for example, a solid rod (not shown). In this regard, it is not possible to add any additional constituents to this chamber and/or connect this chamber to a patient's administration line such that the chamber 14 cannot be adapted to deliver its constituents to the patient.

In an embodiment, the transfer of product within the multi-chamber bag 10 is thereby initiated from the second chamber 14 to the first chamber 12 such that the components of each chamber can be properly mixed to form the bicarbonate-based solution of the present invention. In this regard, the first chamber 12 is larger in volume than the second chamber 14 such that the components of each chamber can be properly mixed once the transfer from the second chamber to the first chamber has occurred. Thus, the multi-chamber bag 10 can house at least two non-compatible solutions that after mixture will result in a ready-to-use dialysis solution. An example of the multi-chamber container is set forth in U.S. Pat. No. 5,431,496, the disclosure of which is incorporated herein by reference. The multi-chamber bag can be made from a gas permeable material, such as polypropylene, polyvinyl chloride or the like.

It should be appreciated that the multi-chamber bag can be manufactured from a variety of different and suitable materials and configured in a number of suitable ways such that the bicarbonate-based solution of the present invention can be effectively formulated and administered to the patient during medical therapy. For example, the second chamber can be larger in volume than the first chamber such that the bicarbonate-based solution of the present invention can be readily and effectively made and administered to the patient from the second chamber.

Although the multi-chamber container disclosed herein is designed to be used for any medical procedure that requires bicarbonate, the embodiment illustrated in FIG. 1 is conveniently used for dialysis therapy including, for example, continuous renal replacement therapy. To this end, in an embodiment, the components of the bicarbonate-based solution of the present invention are separately housed in either of the first chamber 12 and the second chamber 14 such that a mixed solution of the components of the first chamber 12 and the second chamber 14 can be sterilely and readily formed upon mixing within the multi-chamber container.

In an embodiment, the first chamber 12 contains a bicarbonate concentrate and the second chamber 14 contains an electrolyte concentrate. The bicarbonate and electrolyte concentrates can include any variety of different and suitable constituents in varying and suitable amounts such that, when mixed, a desirable and suitable bicarbonate based solution can be formed. In an embodiment, the bicarbonate concentrate includes sodium chloride (NaCl), sodium hydroxide (NaOH), sodium bicarbonate (NaHCO$_3$), the like or suitable combinations thereof, and the electrolyte concentrate includes hydrated calcium chloride (CaCl$_2$.2H$_2$O), hydrated magnesium chloride (MgCl$_2$.6H$_2$O), sodium chloride (NaCl), potassium chloride (KCl), glucose including, for example, anhydrous glucose or dextrose, hydrous glucose or dextrose, the like or suitable combinations thereof.

It should be appreciated that the bicarbonate and electrolyte concentrates can include any suitable pH such that a physiological acceptable pH of the final or reconstituted bicarbonate-based solution can be achieved. In an embodiment, the bicarbonate-based solution can be formulated under moderate or extreme pH conditions. It should be appreciated that the bicarbonate-based solution can be formulated in any suitable manner under moderate or extreme pH conditions.

For example, in an embodiment, the bicarbonate-based solution can be formulated under extreme pH conditions as disclosed in U.S. Pat. No. 6,309,673, the disclosure of which is incorporated herein by reference. Such a formulation allows the product to be packaged without an over pouch.

In an embodiment, the bicarbonate-based solution of the present invention is formulated under moderate pH conditions. Preferably, such a product is placed in a container that includes a gas barrier over pouch.

Under moderate pH conditions, the bicarbonate-based solution of the present invention is formulated by the mixing of a bicarbonate concentrate with a pH ranging from about 7.2 to about 7.9, preferably from about 7.4 to about 7.6, and an electrolyte concentrate with a pH ranging from about 3.0 to about 5.0, preferably from about 4.3 to about 4.5. Under extreme pH conditions, a bicarbonate concentrate with a pH ranging from about 8.6 to about 9.5, preferably from about 8.9 to about 9.0, is mixed with an electrolyte concentrate having a pH that ranges from about 1.7 to about 2.2, preferably about 1.9.

A variety of different and suitable acidic and/or basic agents can be utilized to adjust the pH of the bicarbonate and/or electrolyte concentrates. For example, a variety of inorganic acids and bases can be utilized including hydrochloric acid, sulfuric acid, nitric acid, hydrogen bromide, hydrogen iodide, sodium hydroxide, the like or combinations thereof.

As previously discussed, the present invention provides method and systems for effectively providing a bicarbonate containing solution to a patient during medical therapy. In an embodiment, the present invention can be effectively utilized to treat acute renal failure, particularly with respect to critically ill patients in an intensive care setting. In this regard, Applicants have uniquely discovered that the present invention can provide ready-to-use bicarbonate-based solutions that can be effectively and sterilely administered to the patient during therapy. The ready-to-use formulations can include a number of integrated mechanisms to facilitate the safe and effective use of the bicarbonate-based solutions of the present invention during medical therapy.

In an embodiment, the bicarbonate concentrate and the electrolyte concentrate include a physiological acceptable amount of sodium. To achieve the physiological acceptable level of sodium, the sodium chloride content can be distributed between the bicarbonate concentrate and the electrolyte concentrate such that each contains an equimolar and physiological acceptable concentration of sodium.

In an embodiment, the equimolar amount of sodium is about 160 mmol/L or less. In an embodiment, the equimolar amount of sodium is about 100 mmol/L or more. In an embodiment, the equimolar amount sodium ranges from about 100 mmol/L to about 160 mmol/L, preferably from about 130 mmol/L to about 150 mmol/L, more preferably about 140 mmol/L. In this regard, if the concentrates remain unmixed prior to patient administration (i.e., the frangible connector remains unbroken), this would necessarily ensure that the patient is not overloaded with sodium through the administration of, for example, the bicarbonate concentrate which can be directly coupled to the patient.

As previously discussed, the first chamber 12 of the multi-chamber bag 10 contains the bicarbonate concentrate. In an embodiment, the bicarbonate concentrate includes a physiological acceptable buffered solution of bicarbonate. This ensures that the patient is not overloaded with a number of electrolytes if, for example, the bicarbonate concentrate is separately and mistakenly administered to the patient. This can occur if the frangible connector remains unbroken and, thus, the bicarbonate concentrate and electrolyte concentrate are not mixed prior to administration to the patient where the bicarbonate concentrate is contained in a chamber which is directly coupled to the patient.

In an embodiment, potassium is solely contained in a chamber of the multi-chamber container of the present invention which physically cannot be placed in direct access to the patient. In this regard, the potassium cannot be placed in direct fluid communication with the patient without mixing with the other components of the solution. For example, in an embodiment, the bicarbonate concentrate which can be placed in direct fluid communication with the patient does not contain potassium, such as potassium derived from, for example, potassium chloride or the like. In an embodiment, the potassium chloride is contained solely in the electrolyte concentrate to ensure that the patient cannot receive an undesirable concentration thereof if, by chance, the bicarbonate concentrate and the electrolyte concentrate were not mixed prior to patient administration. In this regard, the bicarbonate-based solution of the present invention can be configured such that the patient cannot receive the electrolyte concentrate directly but rather as a part of a mixed solution of the bicarbonate concentrate and the electrolyte concentrate.

It should be appreciated that a variety of suitable and additional configurations of the present invention can be utilized to facilitate the safe and effective administration of the bicarbonate-based solution to a patient during therapy. In an embodiment, any physiological acceptable amounts of one or more electrolytes can be contained within a chamber of the multi-chamber container (e.g., the first chamber 12 of the multi-bag container 10 as discussed above) of the present invention which can be placed in direct access or fluid communication with the patient. For example, the chamber that can be placed in direct fluid communication with the patient can include a physiological acceptable amount of potassium, sodium, the like or combinations thereof. In an embodiment, the chamber that can be placed in direct access or fluid communication with the patient does not include potassium or the like. In an embodiment, the chamber that can be placed in direct access or fluid communication with the patient houses the bicarbonate concentrate of the present invention.

In an embodiment, each of the bicarbonate concentrate and the electrolyte concentrate include a physiological acceptable amount of potassium prior to mixing such that the resultant solution of bicarbonate and electrolyte concentrates contains a desirable and suitable level of potassium ranging from about 0.1 mmol/L to about 5 mmol/L.

By way of example, and not limitation, the following examples identify a variety of bicarbonate-based solutions made pursuant to an embodiment of the present invention.

EXAMPLE ONE

TABLE 1A

| mmol/L | Formulation 1 | Formulation 2 | Formulation 3 |
|---|---|---|---|
| $Na^+$ | 140 | 140 | 140 |
| $K^+$ | 0 | 2 | 4 |
| $Ca^{++}$ | 1.75 | 1.75 | 1.75 |
| $Mg^{++}$ | 0.5 | 0.5 | 0.5 |
| $Cl^-$ | 109.5 | 111.5 | 113.5 |
| $HCO_3^-$ | 35 | 35 | 35 |
| Anhydrous dextrose | 0 | 5.55 | 5.55 |

TABLE 1B

| g/L | Formulation 1 | Formulation 2 | Formulation 3 |
|---|---|---|---|
| $Na^+$ | 6.14 | 6.14 | 6.14 |
| $Ca^{++}$ | 0.257 | 0.257 | 0.257 |
| $Mg^{++}$ | 0.102 | 0.102 | 0.102 |
| $K^+$ | 0 | 0.149 | 0.298 |
| $HCO_3^-$ | 2.94 | 2.94 | 2.94 |
| Anhydrous dextrose | 0 | 1.0 | 1.0 |
| or hydrous dextrose | 0 | 1.1 | 1.1 |

TABLE 1C

| | Formulation 1 | Formulation 2 | Formulation 3 |
|---|---|---|---|
| Small chamber (g/L) (vol = 906 mL) | | | |
| NaCl | 8.18 | 8.18 | 8.18 |
| $CaCl_2.2H_2O$ | 0.710 | 0.710 | 0.710 |
| $MgCl_2.6H_2O$ | 0.280 | 0.280 | 0.280 |
| KCl | 0 | 0.411 | 0.822 |
| Anhydrous dextrose | 0 | 2.76 | 2.76 |
| or hydrous dextrose | 0 | 3.03 | 3.03 |
| (mmol/L) | | | |
| NaCl | 140 | 140 | 140 |
| $CaCl_2.2H_2O$ | 4.83 | 4.83 | 4.83 |
| $MgCl_2.6H_2O$ | 1.38 | 1.38 | 1.38 |
| KCl | 0 | 5.52 | 11.0 |
| Anhydrous dextrose | 0 | 5.55 | 5.55 |

TABLE 1D

| | Formulation 1 | Formulation 2 | Formulation 3 |
|---|---|---|---|
| Large chamber (g/L) (vol = 1594 mL) | | | |
| NaCl | 4.97 | 4.97 | 4.97 |
| $NaHCO_3$ | 4.61 | 4.61 | 4.61 |
| (mmol/L) | | | |
| NaCl | 85.1 | 85.1 | 85.1 |
| $NaHCO_3$ | 54.9 | 54.9 | 54.9 |

TABLE 1E

| | Measured pH |
|---|---|
| Small Chamber (electrolyte) | 4.3–4.5 |
| Large Chamber (buffer) | 7.4–7.6 |
| Mixed solution | 7.2–7.3 |

Example one identifies three different formulations of the bicarbonate-based solution pursuant to an embodiment of the present invention. Tables 1A and 1B illustrate the final or reconstituted formulations of the bicarbonate-based solution in mmol/L (Table 1A) or g/L (Table 1B).

Table 1C illustrates the content of the electrolyte concentrate associated with each formulation prior to mixing with the bicarbonate concentrate (g/L in top portion of Table 1C and mmol/L in bottom portion of Table 1C). Table 1D illustrates the content of the bicarbonate concentrate associated with each formulation prior to mixing with the electrolyte concentrate (g/L in top portion of Table 1D and mmol/L in bottom portion of Table 1D). Table 1E illustrates the measured pH under moderate pH conditions of the mixed solution (e.g., formulations 1–3), the pH of the small chamber prior to mixing (e.g., the electrolyte concentrate) and the pH of the large chamber prior to mixing (e.g., the bicarbonate concentrate).

EXAMPLE TWO

TABLE 2A

| | Formulation 1 | Formulation 2 | Formulation 3 |
|---|---|---|---|
| Small chamber (g/L) (vol = 1125 mL) | | | |
| $NaHCO_3$ | 13.4 | 13.4 | 13.4 |
| NaOH | 0.520 | 0.520 | 0.520 |
| (mmol/L) | | | |
| $NaHCO_3$ | 160 | 160 | 160 |
| NaOH | 13 | 13 | 13 |

TABLE 2B

| | Formulation 1 | Formulation 2 | Formulation 3 |
|---|---|---|---|
| Large chamber (g/L) (vol = 3375 mL) | | | |
| $CaCl_2.2H_2O$ | 0.343 | 0.343 | 0.343 |
| $MgCl_2.6H_2O$ | 0.136 | 0.136 | 0.136 |
| NaCl | 7.54 | 7.54 | 7.54 |
| KCl | 0 | 0.199 | 0.397 |
| Anhydrous dextrose | 0 | 1.33 | 1.33 |
| or hydrous dextrose | 0 | 1.46 | 1.46 |
| HCl | 0.401 | 0.401 | 0.401 |
| (mmol/L) | | | |
| $CaCl_2.2H_2O$ | 2.33 | 2.33 | 2.33 |
| $MgCl_2.6H_2O$ | 0.667 | 0.667 | 0.667 |
| NaCl | 129 | 129 | 129 |
| KCl | 0 | 2.67 | 5.33 |
| Anhydrous.dextrose | 0 | 7.40 | 7.40 |
| HCl | 11 | 11 | 11 |

TABLE 2C

| | Measured pH |
|---|---|
| Small Chamber (buffer) | 8.9–9.0 |
| Large Chamber (electrolyte) | 1.9 |
| Mixed solution | 7.1–7.3 |

Example two illustrates an example of Formulations 1–3 (See, Tables 1A and 1B) prepared by mixing a bicarbonate concentrate and an electrolyte concentrate under extreme pH conditions pursuant to an embodiment of the present invention.

Table 2A illustrates the content of the bicarbonate concentrate associated with each formulation prior to mixing with the electrolyte concentrate (g/L in top portion of Table 2A and mmol/L in bottom portion of Table 2A). Table 2B illustrates the content of the electrolyte concentrate associated with each formulation prior to mixing with the bicarbonate concentrate (g/L in top portion of Table 2B and mmol/L in bottom portion of Table 2B). Table 2C illustrates the measured pH under extreme pH conditions of the mixed solution (e.g., formulations 1–3), the pH of the small chamber prior to mixing (e.g., the bicarbonate concentrate) and the pH of the large chamber prior to mixing (e.g., the electrolyte concentrate).

It should be understood that various charges and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A two part dialysis solution comprising:
   a bicarbonate concentrate; and
   an electrolyte concentrate, wherein the bicarbonate concentrate and the electrolyte concentrate include a physiological amount of sodium ranging from 100 mmol/L to 173 mmol/L, and wherein the two part dialysis solution does not include acetate, wherein a mixed solution of the bicarbonate concentrate end the electrolyte concentrate further comprises about 0 mmol/L to about 2.0 mmol/L of calcium, about 0 mmol/L to about 1.5 mmol/L of magnesium, about 0 mmol/L to about 5 mmol/L of potassium, about 20 mmol/L to about 45 mmol/L of bicarbonate, about 70 mmol/L to about 130 mmol/L of chloride, about 0 mmol/L to about 45 mmol/L of lactate, and about 0 g/L to about 2.5 g/L of anhydrous glucose.

2. The two putt dialysis solution of claim 1, wherein the bicarbonate concentrate is stored in a first chamber of a multi-chamber container and the electrolyte concentrate is stored in a second chamber of the multi-chamber container.

3. The two part dialysis solution of claim 1, wherein the two part dialysis solution is a hemodialysis solution.

4. The two part dialysis solution of claim 1, wherein the two part dialysis is a solution is a continuous renal replacement therapy solution.

5. The two part dialysis solution of claim 1, wherein the two part dialysis solution is an infusion solution.

6. The two part dialysis solution of claim 1, wherein the two part dialysis solution is a peritoneal dialysis solution.

7. A method of providing dialysis to a patient comprising:
   providing a two part dialysis solution not including acetate, the two part dialysis solution comprising a bicarbonate concentrate and an electrolyte concentrate wherein the bicarbonate concentrate and the electrolyte concentrate include a physiological amount of sodium ranging from 100 mmol/L to 173 mmol/L;
   mixing the bicarbonate concentrate and the electrolyte concentrate to form a mixed solution; and
   using the mixed solution during dialysis, wherein the mixed solution further includes about 0 mmol/L to about 2.0 mmol/L of calcium, about 0 mmol/L to about 1.5 mmol/L of magnesium, about 0 mmol/L to about 5 mmol/L of potassium, about 20 mmol/L to about 45 mmol/L of bicarbonate, about 70 mmol/L to about 130 mmol/L of chloride, about 0 mmol/L to about 45 mmol/L of lactate, and about 0 g/L to about 2.5 g/L of anhydrous glucose.

8. The method of claim 7, wherein the mixed solution is used during hemodialysis.

9. The method of claim 7, wherein the mixed solution is used during continuous renal replacement therapy.

10. The method of claim 7, wherein the mixed solution is infused into the patient as an infusion solution.

11. The method of claim 7, wherein the mixed solution is used during peritoneal dialysis.

* * * * *

UNITED STATES PATENT AND TRADEMARK OFFICE
CERTIFICATE OF CORRECTION

| | | |
|---|---|---|
| PATENT NO. | : 7,122,210 B2 | Page 1 of 1 |
| APPLICATION NO. | : 10/044234 | |
| DATED | : October 17, 2006 | |
| INVENTOR(S) | : Elisabettini et al. | |

It is certified that error appears in the above-identified patent and that said Letters Patent is hereby corrected as shown below:

On Title Page, Item (56) On page 2, add the following information under OTHER PUBLICATIONS:

--Mehta et al., Regional citrate anticoagulation for continuous arteriovenous hemodialysis in critically ill patients, Kidney International, Vol. 38 (1990), pp. 976-981.--

Signed and Sealed this

Sixteenth Day of January, 2007

JON W. DUDAS
*Director of the United States Patent and Trademark Office*